United States Patent [19]

Spielvogel et al.

[11] Patent Number: 5,362,732
[45] Date of Patent: Nov. 8, 1994

[54] BORONATED COMPOUNDS

[75] Inventors: Bernard F. Spielvogel, Raleigh; Anup Sood, Durham; Iris H. Hall, Carrboro; Barbara R. Shaw; Jenó Tomasz, both of Durham, all of N.C.

[73] Assignees: University of North Carolina at Chapel Hill, Chapel Hill; Boron Biologicals, Raleigh; Duke Unversity, Durham, all of N.C.

[21] Appl. No.: 909,950

[22] Filed: Jul. 7, 1992

Related U.S. Application Data

[63] Continuation-in-part of Ser. No. 453,311, Dec. 20, 1989, Pat. No. 5,130,302.

[51] Int. Cl.[5] .................. A61K 31/505; A61K 31/52; C07D 239/00; C07D 473/00
[52] U.S. Cl. ........................... 514/256; 514/261; 514/269; 514/824; 514/825; 514/886; 544/242; 544/264
[58] Field of Search .............. 514/45, 46, 47, 48, 514/49, 50, 51, 64, 886, 824, 825, 269; 536/22.1, 27.1, 28.1, 27.21, 27.6, 27.63, 17.1; 544/242, 264

[56] References Cited

U.S. PATENT DOCUMENTS 4,199,574 4/1980 Schaeffer .................. 514/45
5,130,302 7/1992 Spielvogel et al. .................. 514/45

OTHER PUBLICATIONS

"Boron-Containing Nucleic Acids: Synthesis of Cyanoborane Adducts of 2'-Deoxynucleosides"; *J. Am. Chem. Soc.;* Sood, et al.; 1989, 111, pp. 9234–9235.
"From Boron Analogues of Amino Acids to Boronated DNA: Potential New Pharmaceuticals and Neutron Capture Agents"; *Pure & Appl. Chem.,* Spielvogel, et al.; vol. 63, No. 3, pp. 415–418, 1991.
"Boron-Containing Nucleic Acids. 2.[1] Synthesis of Oligodeoxynucleoside Boranophosphates"; *J. Am. Chem. Soc.;* Sood, et al.; 1990, pp. 9000–9001.
"The Synthesis and Antineoplastic Activity of 2'-Deoxynucleoside-cyanoboranes in Murine and Human Culture Cells"; Sood, et al.; *Anticancer Research*; 12: pp. 335–344 (1992).

*Primary Examiner*—John W. Rollins
*Attorney, Agent, or Firm*—Bell, Seltzer, Park & Gibson

[57] ABSTRACT

A novel class of pharmaceutically active boronated compounds are provided. The boronated compounds include boronated purine and pyrimidine bases and boronated nucleosides, as well as phosphate esters and oligomers thereof. The compounds are boronated at the ring nitrogen of the purine or pyrimidine base, or at a 2', 3' or 5' amino substituent of the nucleoside sugar.

30 Claims, No Drawings

BORONATED COMPOUNDS

RELATED APPLICATIONS

This application is a continuation-in-part of copending U.S. patent application Ser. No. 07/453,311, filed Dec. 20, 1989, now U.S. Pat. No. 5,130,302, the disclosure of which is incorporated by reference herein in its entirety.

FIELD OF THE INVENTION

This invention pertains to novel boron containing compounds having pharmaceutical activity. More specifically, compounds of the present invention include boronated bases, nucleosides and nucleotides having antihyperlipidemic, antiinflammatory, and analgesic activity.

BACKGROUND OF THE INVENTION

Antimetabolites are a well known class of antineoplastic agents that function by interfering with nucleic acid synthesis and consequently, replication within the target cells. Some of these compounds structurally mimic biosynthetic precursors of the naturally occurring nucleic acids, which are essential for replication and cell survival. By replacing these precursors, but without exhibiting the same biological effect, these compounds disrupt replication resulting in the demise of the target cell.

Many antimetabolites have significant antiviral and antitumor activity and are incorporated in a variety of therapeutic regimens. But despite the therapeutic benefits of such compounds, their use is often accompanied by deleterious side effects, e.g. nausea, alopecia, and bone marrow depression. Accordingly, a great deal of interest has focused on synthesizing new analogues with improved therapeutic indexes.

We have recently discovered that boron containing nucleotides may be one class of improved nucleic acid analogues. Some exemplary boronated nucleotides are described in commonly owned U.S. Pat. No. 5,177,198 of B. Spielvogel, A. Sood, I. Hall, and B. Ramsay-Shaw titled "Oligoribonucleoside and Oligodeoxyribonucleoside Boranophosphates" and filed Nov. 30, 1989, which is incorporated herein by reference. There we describe, for example, boronated oligonucleotides that contain a boron functionality attached to internucleotide phosphorus.

Boron containing compounds are also useful in an antineoplastic regimen known as Boron Neutron Capture Therapy (BNCT). Soloway, A. H., *Progress in Boron Chemistry;* Steinberg, H., McCloskey, A. L. Eds.; the Macmillan Company: New York, 1964; Vol. 1, Chapter 4, 203–234. BNCT requires two components (Boron-10 and low energy thermal neutrons) for a radiotoxic reaction. The inherent advantage is that each component can be manipulated independently to produce the desired radiation effect. Boron-10 has a high cross section for thermal neutrons and after neutron capture, the particles generated, Li and α, are relatively large by radiation standards and thus have a relatively short track in tissue, 10–14 microns. The Boron-10 is non-radioactive and for use in BNCT, its compounds do not have to be cytotoxic towards tumor cells. Thermal neutrons have such low energy that they cannot ionize boron components per se. Upon neutron capture, however, the energy generated is sufficient to destroy the cell. The problem in making this procedure clinically effective has stemmed not from the concept, per se, but from lack of knowledge in medicinal chemistry, nuclear engineering and physics, immunology, physiology and pharmacology. The present invention arose from our continued research on new boron-containing compounds having pharmaceutical activity.

SUMMARY OF THE INVENTION

The present invention provides novel boronated compounds, i.e., boronated purine and pyrimidine bases, nucleosides, nucleotides, and oligonucleotides. The compounds of the invention are N-boronated with a boron-containing substituent selected from the group consisting of $-BH_2CN$, $-BH_3$, $-BF_3$, $-BH_2COOR$ and $-BH_2C(O)NHR$, wherein R is hydrogen or a $C_1$ to $C_{18}$ alkyl.

A first embodiment of the present invention is a boronated purine or pyrimidine base which is N-boronated with a boron-containing substituent.

A second embodiment of the present invention is a boronated nucleoside which is N-boronated on the nucleoside base. The boronated nucleoside comprises D-arabinose and a boron-containing substituent.

A third embodiment of the invention is a boronated nucleoside comprising a sugar having at least one 2', 3', or 5' amino substituent, and wherein the sugar is N-boronated at the amino substituent with a boron-containing substituent.

A fourth embodiment of the invention is a boronated nucleoside which is N-boronated on the nucleoside base and comprises a carbocyclic sugar moiety.

The present invention also provides boronated nucleotides comprising a 5' phosphate ester of a boronated nucleoside as described above, and boronated oligonucleotides comprising a chain of natural or modified ribonucleotides or deoxyribonucleotides, at least one nucleotide of which comprises a boronated nucleotide.

Boronated compounds of the present invention have pharmaceutical activity, including antihyperlipidemic, antiinflammatory, and analgesic, activity. Nucleotides of the present invention are useful as intermediates for making oligonucleotides of the present invention.

A method for synthesizing N-boronated compounds of the present invention is also disclosed. The method comprises boronating the compound by the reaction of the compound with a compound selected from the group consisting of polymeric $BH_2CN$ and LX in a polar non-protic solvent, wherein L is a Lewis base and X is a boron-containing substituent selected from the group consisting of $-BH_2CN$, $-BH_3$, $-BF_3$, $-BH_2COOR$ and $-BH_2C(O)NHR$,

DETAILED DESCRIPTION OF THE INVENTION

The present invention provides novel pharmaceutical agents, i.e., boronated purine and pyrimidine bases, nucleosides, and nucleotides, methods for their synthesis, methods for treating patients, and pharmaceutical formulations comprising such agents. The compounds of the invention are N-boronated with a boron-containing substituent selected from the group consisting of $-BH_2CN$, $-BH_3$, $-BF_3$, $-BH_2COOR$ and $-BH_2C(O)NHR$, wherein R is hydrogen or a $C_1$ to $C_{18}$ alkyl. The boronated compounds exhibit antiinflammatory, antihyperlipidemic and analgesic properties.

The term "nucleotide" is a term well-known in the art which is used to refer to the monomeric units of nucleic acids. Typically, nucleotides are described as compounds comprising a nitrogenous heterocyclic base, which is a derivative of either pyrimidine or purine; a sugar such as a pentose; and a molecule of phosphoric acid. The major nucleotides are deoxyribonucleotide (i.e., DNA) and ribonucleotide (i.e., RNA).

The compounds within each of the two major types of nucleotides DNA and RNA differ from each other in their nitrogenous bases. The base components of nucleotides are discussed in more detail below. The two types of nucleic acids also differ with regard to their pentose components. For example, deoxyribonucleotides contain as their pentose component 2'-deoxy-D-ribose, whereas ribonucleotides contain D-ribose. Both sugars occur as furanose forms in nucleotides.

In nucleotides, the pentose is joined to the base by a β-N-glycosyl bond between carbon atom 1 of the pentose and nitrogen atom 9 of the purine bases or nitrogen atom 1 of pyrimidine bases. The phosphate group of nucleotides is in ester linkage with carbon 5 of the pentose. When the phosphate group of a nucleotide is removed by hydrolysis, the remaining structure is known in the art as a nucleoside. Thus, typically the term "nucleoside" refers to a purine or pyrimidine base, and analogues thereof, linked to a pentose. Nucleosides, therefore, have the same structure as nucleotides with the phosphate group absent.

The two classes of nitrogenous bases found in nucleotides are the heterocyclic compounds pyrimidine and purine. Three pyrimidine derivatives, uracil, thymine, and cytosine and two purine derivatives adenine and guanine constitute the major nitrogenous bases found in nucleotides. Adenine, guanine, cytosine and thymine are the bases characteristic of the deoxyribonucleotide units. Similarly, adenine, guanine, cytosine and uracil are the major base components of ribonucleotide units.

In one embodiment of the invention, boronated purine or pyrimidine bases are provided. The term "purine or pyrimidine bases" refers to the bases described above, including purine and pyrimidine, as well as analogs thereof, such as derivatives comprising alkyl, acetyl, isopentyl and hydroxymethyl substituents. Accordingly, the boronated bases of the invention may generally be a natural base, such as adenine, thymine, cytosine, guanine, uracil, xanthine, or hypoxanthine, (the latter two being the natural degradation products) or an analog thereof as found in, for example, 4-acetylcytidine; 5-(carboxyhydroxylmethyl) uridine; 2'-o-methylcytidine; 5-carboxymethylaminomethyl-2-thiouridine; 5-carboxymethylaminomethyluridine; dihydrouridine; 2'-o-methylpseudo-uridine; beta,D-galactosylqueosine; 2'-o-methylguanosine; N6-isopentenyladenosine; 1-methyladenosine; 1-methylpseudo-uridine; 1-methylguanosine; 1-methylinosine; 2,2-dimethylguanosine; 2-methyladenosine; 2-methylguanosine; 3-methyl-cytidine; 5-methylcytidine; N6-methyladenosine; 7-methylguanosine; 5-methylaminomethyluridine; 5-methoxyamino-methyl-2-thiouridine; beta,D-mannosylqueosine; 5-methoxy-carbonylmethyluridine; 5-methoxyuridine; 2-methylthio-N6-isopentenyladenosine; N-((9-beta-D-ribofuranosyl-2-methylthiopurine-6-yl) carbamoyl) threonine; N-((9-beta-D-ribofuranosyl-purine-6-yl) N-methyl-carbamoyl)threonine; uridine-5-oxyacetic acid methylester; uridine-5-oxyacetic acid (V); pseudouridine; queosine; 2-thiocytidine; 5-methyl-2-thiouridine; 2-thiouridine; 4-thiouridine; 5-methyluridine; 2'-o-methyl-5-methyluridine; and 2'-o-methyluridine.

Other illustrative bases which may be provided in boronated form in accordance with the present invention include 9-hydroxyethylmethyl and related derivatives of 6- and 2,6-substituted purines as disclosed in U.S. Pat. No. 4,199,574, the disclosure of which is incorporated herein by reference. The substituted purines have the formula:

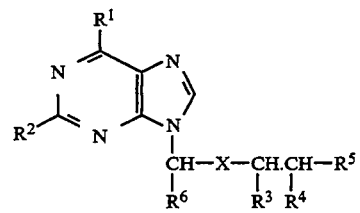

wherein X is oxygen or sulphur; $R^1$ is hydrogen, halogen, hydroxy, alkoxy, azide, thio, alkylthio, amino, alkylamino, or dialkylamino; $R^2$ is hydrogen, halogen, alkylthio, acylamino, amino or azide; $R^3$ is hydrogen, straight or branch chain or cyclic alkyl, hydroxyalkyl, benzyloxyalkyl, or phenyl; $R^4$ is hydrogen, hydroxy, or alkyl; $R^5$ is hydrogen, hydroxy, amino, alkyl, hydroxyalkyl, benzyloxy, benzoyloxy, benzoyloxymethyl, sulphamoyloxy, phosphate carboxypropiamyloxy, straight chain or cyclic acyloxy having from 1 to 8 carbon atoms, e.g., acetoxy or substituted carbamoyl group of formula NHCO-Z wherein Z is alkyl, aryl or aralkyl optionally substituted by one or more of sulphonyl, amino, carbamoyl or halogen; $R^6$ is hydrogen or alkyl, provided that when X is oxygen and $R^2$, $R^3$, $R^4$, and $R^6$ are hydrogen, $R^1$ is not amino or methylamino when $R^5$ is hydrogen or hydroxy, or a salt thereof. The term alkyl is denoted to mean 1 to 12 carbon atoms, and preferably 1 to 8 carbon atoms except for the alkyl content of $R^6$ which when present has from 1 to 8 carbon atoms and in all other cases when the substituents have an alkyl moiety it has from 1 to 4 carbon atoms. A preferred base according to this aspect of the invention is 9-[(2-hydroxyethoxy)methyl]guanine.

Exemplary boronated bases include:
(1) adenine-$N^1$-cyanoborane;
(2) adenine-$N^3$-cyanoborane;
(3) adenine-$N^7$-cyanoborane;
(4) guanine-$N^7$-cyanoborane;
(5) cytosine-$N^3$-cyanoborane;
(6) hypoxanthine-$N^7$-cyanoborane;
(7) 5-methylcytosine-$N^3$-cyanoborane;
(8) 9-benzyladenine-$N^1$-cyanoborane;
(9) 9-ethyladenine-$N^1$-cyanoborane;
(10) 9-[(2-hydroxyethoxy)methyl]guanine-$N^7$-cyanoborane; and
(11) 9-hydroxyethylguanine-$N^7$-cyanoborane.

The boron substituents may be at nitrogen 1, 3, 7 or 9 of the purine base, and at nitrogen 1 or 3 of the pyrimidine base.

In another embodiment of the invention, N-boronated nucleosides are provided. The boronated nucleosides of the invention include the pentose D-arabinose and a base as described above.

Illustrative of boronated nucleosides in accordance with this embodiment of the invention are:
(12) 9-β-D-arabinofuranosyladenine-$N^7$-cyanoborane;
(13) 9-β-D-arabinofuranosyladenine-$N^1$-cyanoborane;

(14) 1-β-D-arabinofuranosylcytosine-N³-cyanoborane;
(15) 9-β-D-arabinofuranosyladenine-N¹-carboxyborane;
(16) 9-β-D-arabinofuranosyladenine-N¹-carbomethoxyborane; and
(17) 9-β-D-arabinofuranosyladenine-N¹-(N-ethylcarbamoyl) borane.

In another embodiment of the invention, boronated nucleosides are provided comprising a carbocyclic sugar and a base as described above. As used herein, the term "carbocyclic sugar" refers to a sugar derivative wherein the oxygen atom in the furanose form of the sugar has been replaced with a carbon atom. Illustrative of boronated nucleosides in accordance with this embodiment of the invention are:

(18) carboadenosine-N¹-cyanoborane;
(19) carboadenosine-N⁷-cyanoborane;
(20) carboguanosine-N⁷-cyanborane;
(21) carbocytosine-N⁷-cyanoborane; and
(22) carboadenosine-N¹-carboxyborane.

In yet another embodiment of the invention, boronated nucleosides are provided wherein the nucleoside sugar component has at least one 2', 3' or 5' amino substituent, and wherein the nucleoside is N-boronated at the amino substituent. The sugar component may be, for example, 2'-deoxy-D-ribose, D-ribose, 2', 3'-deoxy-D-ribose, or D-arabinose. The base may be any of those given above. The base may also be N-boronated as described above. Illustrative of boronated nucleosides in accordance with this embodiment of the invention are:

(23) 3'-deoxy-3'-aminothymidine-3'-N-cyanoborane;
(24) 5'-deoxy-5'-aminothymidine-5'-N-cyanoborane;
(25) 3'-deoxy-3'-aminothymidine-3'-N-carboxyborane;
(26) 2'-aminothymidine-2'N-carboethoxyborane;
(27) 3'-deoxy-3'-aminothymidine-3'N-(N-ethylcarbamoyl)-borane;
(28) 3'-deoxy-3'aminocytidine-N³, 3'N-dicyanoborane;
(29) 3'-deoxy-3'-aminoadenosine-N¹, 3'N-dicyanoborane; and
(30) 5'-deoxy-5'-aminoguanosine-N⁷, 3'N-dicyanoborane.

The nucleosides of the present invention further comprise 5'-phosphate esters of the N-boronated bases and nucleosides described herein. Such phosphate esters are also known as nucleotides, as described above. Such nucleotides, particularly the monophosphates, are protected in conventional manner and used for the syntheses of oligonucleotides, as discussed below. Such phosphate esters include 5' mono-, di- and triphosphates, which may be protected as esters. Additionally, molecules and macromolecules comprising multimers of two or more nucleosides, which may be linked via a 3'-5' phosphate ester, e.g. oligonucleotides (the terms "oligonucleotides" and "polynucleotides", being used interchangeably herein), and comprising one or more N-boronated bases or nucleosides are also the subject of the present invention. Accordingly, N-boronated nucleotides, oligonucleotides, and polynucleotides may be used as therapeutic agents and otherwise useful reagents, e.g. diagnostic reagents.

Oligonucleotides of the present invention can be synthesized in accordance with methods that are well known in the art. Such methods include the phosphite method and the phosphotriester method. 1 Chemistry of Nucleosides and Nucleotides, 294ff (L. Townsend ed. 1988). As will be apparent to those skilled in the art, the position of a nucleotide having at least one 2', 3' or 5' boronated amino substituent as described above is dependent upon which amino substituent is boronated. In other words, nucleotides comprising 3' and 5' boronated amino substituents will be positioned at an end of an oligonucleotide chain. The length of the oligonucleotide is not critical, as modern synthetic techniques and splicing techniques have made synthetic oligonucleotides of considerable length feasible. Thus, the oligonucleotide may for example be 2 to 3 nucleotides long, 2 to 18 nucleotides long, 2 to 30 nucleotides long, 2 to 50 nucleotides long, or 50 or more nucleotides long.

Oligonucleotides containing N-boronated bases or nucleosides may alternatively be prepared, with boronation occurring randomly, in essentially the same manner as the nucleoside, but with an oligonucleotide substituted for the nucleoside. For example, in such a reaction, the 3' terminus of the oligonucleotides may be immobilized to a solid support (e.g., controlled pore glass), the 5' terminus protected as the dimethyltrityl ether, and amino groups on bases protected with isobutyryl groups.

Yet another method of synthesizing boronated oligonucleotides in accordance with the invention is by enzymatic incorporation of a boronated nucleosidetriphosphate into an oligonucleotide using enzymes known in the art as polymerases.

Derivatives of the oligonucleotides and polynucleotides may additionally be formed by modifying the internucleotide phosphodiester linkage. Internucleotide phosphodiester linkages in the chain are modified, for example, to the methylphosphonate, the phosphotriester, the phosphorothiaote, the phosphorodithioate, and the phosphoramidate, all as is known in the art.

Additional synthetic analogues of the nucleosides, nucleotides, and oligonucleotides of the present invention may be formed by otherwise modifying the 3' or 5' end of the nucleoside, and any 2' hydroxyl groups. Groups that can be added to the 3' or 5' end vary widely, from relatively inert protecting groups to reactive groups or groups with special properties to obtain desirable physical, chemical, or biochemical effects.

A wide variety of protecting groups can be substituted on the 2', 3', and 5' hydroxy groups, such as the triphenylmethyl (trityl) group and its derivatives on the 5' hydroxy group, and acetyl, benzoyl, or the 3'-o-succinyl group on the 3' hydroxy group, as is know in the art. See 1 Chemistry of Nucleosides and Nucleotides, 287–92 (L. Townsend ed. 1988). In general, the 5' hydroxy group is protected with an acid labile group and the 3' hydroxy group is protected with an acyl group. Id. at 289 (When the 5' hydroxyl group is protected with an acid labile group such as mono- and dimethoxytrityl, the 3'-hydroxyl group of deoxynucleosides can be protected with acyl groups). In general, a 2' hydroxy group is protected as a methyl ether, protected with a silyl group, or the 2' and 3' hydroxy groups may be protected together as an acetal.

Nucleosides, nucleotides and oligonucleotides may also be protected at the base, for example, at the amino group of guanine, cytidine, and adenine, or the carbonyl group of guanine, hypoxanthine, uracil, or thymine. A wide variety of base protecting groups are known in the art and are readily available.

Reactive groups or groups with special properties may also be attached at the 3' or 5' position. For example, analogs may be formed by joining an intercalating agent to oligonucleotides and polynucleotides in the manner described in U.S. Pat. No. 4,835,263 to Nguyen et al. (the disclosure of this and all other patent references cited herein is incorporated by reference).

The invention also provides methods for preparing the boronated compounds. The purine and pyrimidine bases, nucleosides and nucleotides described above are boronated via a one-step process wherein the compound to be boronated is reacted with an organoborane in a nonprotic polar solvent. The organoborane is generally either polymeric $BH_2CN$ or a compound LX, wherein L is a Lewis base and X is a boron-containing substituent as given above. As will be apparent to those skilled in the art, polymeric $BH_2CN$ includes oligomers thereof such as trimers, pentamers, decamers, and the like. Suitable Lewis bases include amine, phosphine, sulfide, and ether (e.g., tetrahydrofuran). Exemplary organoboranes include aniline-cyanoborane, triphenylphosphine-carboalkoxyboranes, (wherein the alkoxy group alkyl is R as given above), dimethylsulfide-borane, and tetrahydrofuran-borane. A preferred organoborane is triphenylphosphine-cyanoborane. Suitable solvents include N,N-dimethyl formamide (DMF).

The reaction takes place for a time sufficient so that an equilibrium is reached. The reaction temperature is selected so that the compound to be boronated is sufficiently soluble in solvent, i.e., at a temperature of about room temperature to about 60° C. For example, compounds having the base guanine as a component are typically less soluble and thus may require higher process temperatures.

The method of the invention is susceptible to numerous variations. For example, the boronated bases according to the invention may be prepared by directly boronating the base as described above. Alternatively, the boronated bases may be prepared by providing a boronated nucleoside having as a component the desired boronated base and cleaving the glycosidic bond of the nucleoside. Such glycosidic cleavage may be, for example, by acidic or enzymatic hydrolysis.

In another variation, boronated compounds having uracil or hypoxanthine base components are synthesized. In this aspect of the invention, the compound to be boronated comprises a purine or pyrimidine base having an amino substituent, such as adenine or cytosine. The compound is boronated as described above and subsequently deaminated by base using techniques known in the art to remove the amino substituent.

The invention also provides a method for preparing boronated nucleosides wherein the nucleoside sugar component has at least one 2', 3' or 5' amino substituent and the nucleoside is N-boronated at the amino substituent. In this embodiment, at least one 2', 3' or 5' hydroxy group of the sugar is replaced with an amino group using any of the techniques known in the art. The sugar is subsequently boronated at the sugar amino substituent group as described above. In one aspect of this invention, the purine or pyrimidine base component of the nucleoside is also boronated as described above, to provide a nucleoside having both a N-boronated sugar amino substituent and an N-boronated base.

The compounds of the present invention have pharmaceutical activity and are useful in treating mammals (e.g., human, cat, dog, cow, horse, mouse) suffering from one or more of several maladies. For example, the compounds of the present invention show cytotoxic activity against colorectal carcinoma, adenocarcinoma, osteosarcoma, breast carcinoma and glioma. Accordingly, the compounds of the present invention provide a method for treating a tumor bearing mammal comprising administering to said mammal a therapeutically effective amount of a boronated nucleoside of the present invention.

The compounds of the present invention also have pharmaceutical activity as antiinflammatory agents in mammals. The compounds of the present invention provides a method for treating a mammal suffering from inflammation comprising administering to said mammal a therapeutically effective amount of an N-boronated nucleoside. The compounds of the present invention may provide additional utility when conjointly administered with other known antiinflammatory agents or pain killers or some such pharmaceutical. Exemplary of other known antiinflammatory agents are acetylsalicylic acid (aspirin), salicylic acid, diflunisal, phenylbutazone, oxyphenbutazone, antipyrine, aminopyrine, dipyrone, apazone, acetaminophen, indomethacin, sulindac, meclofenamate, tolmetin, zomepirac, ibuprofen, and piroxicam.

The compounds of the present invention are useful as hypolipidemic agents. The compounds of the present invention provide a method for treating a mammal suffering from hyperlipidemia comprising administering to said mammal a therapeutically effective amount of an N-boronated nucleoside. Additionally, the compounds of the present invention provide a method for treating a mammal suffering from hypercholesterolemia comprising administering to said mammal a therapeutically effective amount of an N-boronated nucleoside. By administering these compounds to hyperlipidemic patients the total lipoprotein level may be reduced or the lipoprotein profile may be improved. Furthermore, these compounds may be conjointly administered with other known hypolipidemic agents to enhance or supplement their efficacy. Exemplary of such other known hypolipidemic agents are nicotinic acid, clofibrate, gemfibrozil, probucol, cholestyramine, colestipol, compactin, mevinolin, choloxin, neomycin, and beta-sitosterol.

The compounds of the present invention are also useful as analgesic agents. The compounds of the present method provide a method for treating a mammal suffering from pain comprising administering to said mammal a therapeutically effective amount of an N-boronated nucleoside. The compounds of the present invention may provide additional utility when cojointly administered with other known analgesic agents or some such pharmaceutical. Exemplary of other known analgesic agents are acetylsalicylic acid (aspirin), salicylic acid, diflunisal, phenylbutazone, oxyphenbutazone, antipyrine, aminopyrine, dipyrone, apazone, acetaminophen, indomethacin, sulindac, meclofenamate, tolmetin, zomepirac, ibuprofen, and piroxicam.

The compounds of the present invention may be administered in any of the variety of modes currently employed for analogous pharmaceutical agents, which modes are well known in the art. For example, these compounds may be administered systemically. Systemic administration includes parenteral administration and gastro-enteral administration.

When prepared in a pharmaceutical formulation for parenteral administration the compounds of the present invention should be prepared in a pharmaceutically acceptable carrier such as substantially non-pyrogenic, sterile, parenterally acceptable, aqueous solutions.

Alternatively, the compounds of the present invention may be formulated in pharmaceutical preparations for gastro-enteral administration. Such pharmaceutical preparations include tablets, capsules and suppositories. When formulated for administration according to any of the above methods the pharmaceutical preparations may further comprise buffers, binders, and other pharmaceutically acceptable excipients as are well known in the art.

A therapeutically effective amount of a boronated compound of the invention is in the range of about 0.1–100 mg/kg/day. The preferred range is about 0.5–50 mg/kg/day. More preferred is an amount in the range of about 1–10 mg/kg/day. When administered conjointly with other pharmaceutically active agents even less of the boronated nucleoside may be therapeutically effective.

The oligonucleotides of the present invention may be used as probes in a variety of diagnostic technique. One such diagnostic technique is Magnetic Resonance Imaging (MRI). MRI is a noninvasive technique used to detect the presence and location of tumors in a patient. For example, as contemplated in the present context, cancer cell specific boronated compounds are administered to a patient, whereupon they concentrate in cancerous tissue. The MRI instrument is capable of detecting and locating regions of abnormal concentrations of Boron. By indicating the regions having high relative concentrations of Boron, MRI establishes the presence and location of tumors.

Another diagnostic application of the oligonucleotides of the present invention is their use as molecular probes. By incorporating N-boronated nucleosides, or their 5'-phosphate esters, into an oligonucleotide, either at an interior or terminal position, a detectable oligonucleotide probe is constructed that can be used to detect the presence of complementary sequences of DNA or RNA in a sample.

The probes can be used in any suitable environment, such as Southern blotting and Northern blotting, the details of which are know. See, e.g., R. Old and S. Primrose, Principles of Gene Manipulation, 8–10 (3d Ed. 1985). When used a probes, the boron atom serves as a radiolabel, though it is not itself radioactive until exposed to thermal neutron radiation (low energy neutrons). When exposed to low energy neutrons, $^{10}B$ absorbs a neutron and forms $^{11}B$, which rapidly decays and releases an alpha particle, thus providing a detectable signal. The techniques involved in the generation of the alpha particle are known. See, e.g., A. Soloway, Borax Rev. 3, 7–9 (1988).

While the foregoing invention has been described in some detail for purposes of clarity and understanding, it will be clear to one skilled in the art from a reading of this disclosure that various changes in form and detail can be made without departing from the true scope of the invention. In the examples below, g=grams, kg=kilogram, mg=milligram, mm=millimeter, cm=centimeter, nm=nanometer, mmol=millimole, pmol=picamole, M=molar, mM=millimolar, μM=micromolar, mL=milliliter, μs=microsecond, μL=microliter, Hg=mercury, and Å=angstrom.

EXAMPLE 1

Synthesis of $N^1$- and $N^7$-cyanoborano-2'-deoxyadenosines: Reaction of 2'-deoxyadenosine with Triphenylphosphine Cyanoborane 2'-deoxyadenosine (2.5 g, 10 mmol; dried at 110° C. and 1 mm Hg over $P_2O_5$ for 8 hours) was dissolved in N,N-dimethylformamide ("DMF", 100 ml; distilled from $CaH_2$ and stored over 4Å molecular sieves). Triphenylphosphine cyanoborane (10.5 g, 35 mmol) was added to the solution. The suspension was stirred with the exclusion of atmospheric moisture at room temperature. Triphenylphosphine cyanoborane was completely dissolved after 15–17 hours stirring.

The solution was evaporated to dryness (bath temperature 45° C.). The solid residue at evaporation was triturated with dry ethyl ether, filtered by suction and washed with dry ethyl ether (a total amount of about 150 ml of ethyl ether was used).

The precipitate was dissolved in 100 ml DMF. The solution was stirred with the exclusion of atmospheric moisture at room temperature for 4 days. Silica gel (15 g) was added to the solution, and the mixture was evaporated to dryness. The residue was separated by flash chromatography on silica gel (200 g, column diameter 2.5 cm) with a mixture of dichloromethane:methanol (95:5 v/v). Two cleanly separated ultraviolet (UV) absorbing peaks emerged from the column. By combining and evaporating the appropriate fractions, 343 mg (11.3%) of $N^7$-cyanoborano-2'-deoxyadenosine and 1.04 g (34.3%) $N^1$-cyanoborano-2'-deoxyadenosine were obtained from the first and the second peak, respectively.

The results of the elemental analysis of $N^7$-cyanoborano-2'-deoxyandenosine (calculated for $C_{11}H_{15}BN_6O_3 \cdot 0.75H_2O$) are set forth below:

|  | % Carbon | % Hydrogen | % Nitrogen |
| --- | --- | --- | --- |
| calculated | 43.51 | 5.48 | 27.68 |
| found | 43.52 | 5.30 | 27.77 |
| MS, m/z 291(M + H)+ | | | |

| UV | pH 2.0 | pH 7.0 | pH 11.0 |
| --- | --- | --- | --- |
| $\lambda_{max}$(nm) | 266 | 266 | 266 |
| $\lambda_{min}$(nm) | 230 | 230 | 230 |
| $\epsilon_{max}$ | 16,300 | 16,500 | 16,300 |
| $\epsilon_{260}$ | 15,200 | 14,900 | 14,600 |

$^1$H-NMR (DMSO-d$_6$, 300 MHz)

δ(ppm): 9.207 (s, 1H, C(8)-$\underline{H}$), 8.360 (s, 1H, C(2)-$\underline{H}$), 6.403 (t, $^3H_{HH}$=6.0 Hz, 1H, C(1')-$\underline{H}$), two flat, broad peaks between the signals of C(2)-$\underline{H}$ and C(1')$\underline{H}$ protons (2H, N$\underline{H_2}$), 5.365(d, $^3J_{HH}$=4.4 Hz, 1H, C(3')-O$\underline{H}$), 5.166 (t, $^3J_{HH}$=4.5 Hz, 1H, C(5')-O$\underline{H}$), 4.392–4.418 (m, 1H, C(3')-$\underline{H}$), 3.858–3.910 (m, 1H, C(4')-$\underline{H}$) 3.539–3.680 (two m, 2$\underline{H}$, C(5')-$\underline{H_2}$), 2.341–2.493 and 2.682–2.766 (two m, 4H, C(2')-$\underline{H_2}$+B$\underline{H_2}$).

$N^1$-cyanoborano-2'-deoxyadenosine was compared with an authentic specimen.

EXAMPLE 2

Reaction of Nucleosides with Triphenylphosphine Cyanoborane at Elevated Temperatures The following nucleosides (0.1 mmol) in DMF (1–2 ml) were reacted with triphenylphosphine cyanoborane (0.3 mmol) at 37° C. After 36 hours the following yields were detected by HPLC (high performance liquid chromatography) at 260 mm.

| Nucleoside | Yield (%) |
|---|---|
| 2'-deoxyadenosine | 69.6[1] |
| Adenosine | 70.0[2] |
| 2'-deoxycytidine | 20.8[3] |
| Cytidine | ~10.0[4] |
| 2'-deoxyguanosine | 46.2[5] |
| Guanosine | 60.6[6] |
| 2'-deoxyinosine | 33.0 |
| Inosine | 43.4 |

[1]Ratio of $N^1$-cyanoborano-2'-deoxyadenosine to $N^7$-cyanoborano-2'-deoxyadenosine was 2:3.
[2]A mixture of $N^1$-and-$N^7$-cyanoborano-adenosines.
[3]After 122 hours, the yield was 36.8%.
[4]Approximate yield only, because of the partial precipitation of cytidine from the reaction mixture.
[5]A yield of 57.9% was obtained after 66 hours.
[6]The reaction was run at 55° C.

EXAMPLE 3

Synthesis of $N^1$- and $N^7$-carboxyborano-2'-deoxyadenosines: Reaction of 2'-deoxyadenosine with Triphenylphosphine Carboxyborane 2'-deoxyadenosine (125 mg, 0.5 mmol) was dissolved in DMF (5.0 ml). Triphenylphosphine carboxyborane (640 mg, 2.0 mmol) was added, and the suspension was stirred with the exclusion of atmospheric moisture at room temperature for 28 hours.

The reaction mixture was evaporated to dryness. The solid evaporational residue was triturated with ethyl ether, filtered by suction and washed with ethyl ether (total amount of about 25 ml of ethyl ether was used). The solid was resuspended in DMF (5 ml) and stirred with the exclusion of atmospheric moisture at room temperature for an additional 28 hours.

After adding silica gel (1.5 g), the reaction mixture was evaporated to dryness. The evaporational residue was separated by flash chromatography on silica gel (50 g, column diameter 2.5 cm) with a mixture of dichloromethane methanol (90:10 v/v). The two peaks emerged after the 2'-deoxyadenosine peak, were pooled and evaporated to dryness to give 25 mg (16.2%) of $N^7$-carboxyborano-2'-deoxyadenosine (from the closer peak to 2'-deoxyadenosine) and 12.2 mg (7.9%) of $N^1$-carboxyborano-2'-deoxyadenosine (from the farther peak to 2'-deoxyadenosine). The $^1$H-NMR (DMSO-$d_6$, 300 MHz) for each is set forth below:

$N^7$-carboxyborano-2'-deoxyadenosine:

δ(ppm): 10.477 (s, 1H, COO$\underline{H}$), 9.173 (s, 1H, C(8)-H), 8.327 (s, 1H, C(2)-$\underline{H}$), 6.419 (t, $^3J_{HH}$=6.4 Hz, 1H, C(1')-$\underline{H}$), two flat, broad peaks between the signals of C(2)-H & C(1')-H protons (2H, NH$_2$), 5.384 (d, $^3J_{HH}$=3.7 Hz, 1H, C(3')-O$\underline{H}$), 5.167 (t, $^3J_{HH}$=5.1 Hz 1H, C(5')-O$\underline{H}$), 4.400 (unresolved, 1H, C(3')-H, 3.885-3.923 (m, 1$\underline{H}$, C(4')-$\underline{H}$), 3.514–3.685 (m, 2H, C(5')-$\underline{H}_2$) and 2.335–2.877 (two m, 4H, C(2')-$\underline{H}_2$).

$N^1$-carboxyborano-2'-deoxyadenosine:

δ(ppm): 10.236 (broad s, 1H, COO$\underline{H}$), 8.985 (broad s) 1H, N$\underline{H}_2$), 8.581 (s, 1H, C(2)-$\underline{H}$), 8.292 (s, 1H, C(8)-$\underline{H}$), 7.418 (broad s, 1H, N$\underline{H}_2$), 6.358 (t, $^3J_{HH}$=6.6 Hz, 1$\underline{H}$, C(1')-$\underline{H}$), 5.371 (unresolved, 1H, C(3')-O$\underline{H}$), 4.979 (unresolved, 1H, C(5')-O$\underline{H}$), 4.409 (unresolved, 1H, C(3')-$\underline{H}$), 3.850–3.889 (m, 1$\underline{H}$, C(4')-$\underline{H}$), 3.492–3.616 (m, 2H, C(5')-$\underline{H}_2$) and 2.303–2.738 (two m 4H, C(2')-$\underline{H}_2$+B$\underline{H}_2$).

EXAMPLE 4

Synthesis of $N^3$-cyanoborano-adenine: Reaction of Adenine with Triphenylphosphine Cyanoborane Adenine (1.35 g, 10 mmol) was reacted in DMF (100 ml) with triphenylphosphine cyanoborane (9 g, 30 mmol) at 60° C. Aliquots were removed at intervals and analyzed by HPLC at 265 mm. Results are summarized in Table 1 below:

TABLE 1

| Reaction time (hours) | Composition of the reaction mixture (%) | | | | |
|---|---|---|---|---|---|
| | Adenine | $N^3$-cyano-borano-Adenine | $N^1$-cyano-borano-Adenine | $N^7$-cyano-borano-Adenine | $X^1$ |
| 0.5 | 69.4 | 17.9 | 7.2 | 5.5 | <1.0 |
| 1.0 | 46.6 | 29.9 | 12.1 | 8.4 | 3.0 |
| 2.0 | 21.6 | 43.5 | 17.2 | 11.4 | 6.3 |
| 3.0 | 12.6 | 49.3 | 18.5 | 12.1 | 7.5 |

[1]Compound of unknown structure.

The individual compounds were identified by comparing them with authentic samples.

$N^3$-cyanoborano-adenine was obtained from an aliquot of the above mixture by flash chromatography (silica gel, dichloromethane-methanol (95:5 v/v) and analyzed as set forth below:

MS, m/z 175(M+H)$^+$

| UV | pH 2.0 | pH 7.0 | pH 11.0 |
|---|---|---|---|
| $\lambda_{max}$(nm) | 270 | 272 | 272 |
| $\lambda_{min}$(nm) | 234 | 238 | 244 |

$^1$H-NMR(DMSO-$d_6$, 300 MHz). δ(ppm): 13.260 (broad s, 1H, N-$\underline{H}$), 8.617 (s, 1H, N$\underline{H}_2$), 8.390 (s, 1H, C(2)-$\underline{H}$ or C(8)-$\underline{H}$), 8.356 (s, 1H, N$\underline{H}_2$), 8.326 (s, 1H, C(2)-$\underline{H}$ or C(8)-$\underline{H}$), 2.300–2.770 (broad s, 2H, B$\underline{H}_2$).

EXAMPLE 5

Synthesis of $N^7$-cyanoborano-2'-deoxyguanosine-5'-Monophosphate: Reaction of 2'-deoxyguanosine-5'-monophosphate with Triphenylphosphine Cyanoborane 2'-deoxyguanosine-5'-monophosphate (17.8 mg, 0.05 mmol) was suspended in methanol (1.0 ml). Tri-n-butylamine (23.7 ml, 0.1 mmol) was added to the suspension. The solution formed and was evaporated to dryness.

The oily residue was dissolved in DMF (0.5 ml). To the solution triphenylphosphine cyanoborane (60 mg, 0.2 mmol) was added. The reaction mixture was set aside with the exclusion of atmospheric moisture at room temperature for one week. TLC (thin layer chromatography) analysis of the homogeneous reaction mixture showed about 40% conversion of the starting material to $N^7$-cyanoborano-2'-deoxyguanosine-5'-monophosphate (on silica gel in n-propanol: conc. NH$_4$OH:H$_2$O (11:7:2 v/v).

The product was compared with an authentic $N^7$-cyanoborano-2'-deoxyguanosine-5'-monophosphate that had been prepared by phosphorylating $N^7$-cyanoborano-2'-deoxyguanosine according to the Yoshikawa-method.)

EXAMPLE 6

Synthesis of 3'-amino-cyanoborano-thymidine and 3'-deoxy-3'-amino-thymidine-3'N-cyanoborane 3'-aminothymidine (0.25 mg, 1.04 mmol) and triphenylphosphine-cyanoborane (1.25 mg, 4.15 mmol) were taken in anhydrous dimethylformamide (6.2 ml) and were heated at 55° C. for 48 hours. Silica gel was added to this mixture until all of the solution had soaked into it and there was some silica gel left dry.

The mixture was kept under vacuum for 2 days, during which time silica gel had turned back into a free flowing powder. A silica gel column was prepared using $CH_2Cl_2$ as solvent and the reaction mixture adsorbed on dry silica gel was poured on top of the silica gel column. The column was eluted first with $CH_2Cl_2$ (approximately 800 ml), then with $CH_2Cl_2$:MeOH (9.5, 0.5, 1000 ml) and lastly with $CH_2Cl_2$:MeOH (9:1) until all the pure product had eluted.

The fractions containing the pure product were combined and the solvent was removed in vacuo to give a glassy solid. The product was dried in vacuo for 24 hours to give 255 mg (87.9%) of product. The results of $^1H$ NMR and elemental analysis of the product are set forth below:

$^1H$ NMR$_{(D2O)}$: δ(ppm): 7.50 (s, H6); 6.13 (t, 1'H); 4.09 (m, 3'H); 3.75 (m, 5'$CH_2$); 3.54 (q, 4'H); 2.46 (m, 2'$CH_2$); 1.77 (s, $CH_3$(5)); 1.1–1.8 (v.v.br, $BH_2$).

$^{11}B$ NMR$_{(acetone-d6)}$: δ= −24.4 ppm, br.t., $^1J_{B,H} \approx 100$ Hz.

Analysis calculated for $BC_{11}H_{17}N_4O_4$:

|  | % Carbon | % Hydrogen | % Nitrogen |
|---|---|---|---|
| calculated | 47.17 | 6.12 | 20.00 |
| found | 46.93 | 6.24 | 19.78 |

EXAMPLE 7

Synthesis of Acyclovir-$N^7$-cyanoborane

Acyclovir (8.88 mmol) and triphenylphosphine-cyanoborane (11.6 mmol) were suspended in 150 ml dry DMF. The mixture was stirred under inert atmosphere at 65° C. for four days. It was filtered and the residue was washed with methanol. The filtrate was adsorbed onto silica gel and then dried under reduced pressure to remove the solvents. The product was purified by flash chromatography on silica gel using $CH_3CN$:$CH_3OH$ (9:1), $R_f=0.50$. NMR and elemental analysis results of the product is set forth below:

$^1H$ NMR (DMSO-$d^6$): δ(ppm): 2.3 (br.s., 2H, $BH_2$); 3.53 (s, 2H, 3'$CH_2$); 3.57 (q, 2H, 2'-$CH_2$); 4.72 (s, 1H, 3'-OH); 5.46 (s, 2H, 1'-$CH_2$); 6.93 (s, 2H, $NH_2$); 8.79 (s, 1H, H8); 11.21 (s, 1H, NH).

$^{11}B$ NMR (DMSO-$d^6$) δ= −21.9 ppm. IR (nujol): 2423 cm$^{-1}$, ν(BH); 2199 cm$^{-1}$, ν(CN). Elemental analysis calculated for $BC_9H_{13}N_6O_3 \cdot \frac{1}{2} CH_3OH$:

|  | % Carbon | % Hydrogen | % Nitrogen |
|---|---|---|---|
| calculated | 40.74 | 5.40 | 30.00 |
| found | 40.71 | 5.56 | 30.19 |

EXAMPLE 8

Synthesis of $N^1$- and $N^7$-cyanoborano-adenines and $N^7$-cyanoborano-guanine by Acid Hydrolysis of the Respective 2'-deoxyribonucleoside Derivatives Synthesis of $N^1$- and $N^7$-cyanoborano-adenines $N^1$- or $N^7$-cyanoboronated-2'-deoxyadenosine (200 mg) was dissolved in $10^{-2}N$ aqueous hydrochloric acid (50 ml). The clear solutions were set aside at room temperature for 3 days. The separated white crystals were filtered by suction, washed with ice-cold water (2×2 ml) and dried at room temperature and 1 Hg mm over $P_2O_5$ overnight. The yield for $N^1$-cyanoborano-adenine was 80 mg (67%), and the yield for $N^7$-cyanoborano-adenine was 90 mg (75%). Elemental analysis results are set forth below:

$N^1$-cyanoborano-adenine elemental analysis (calculated for $C_6H_7BN_6 \cdot 0.25H_2O$):

|  | % Carbon | % Hydrogen | % Nitrogen |
|---|---|---|---|
| calculated | 40.37 | 4.24 | 47.09 |
| found | 40.61 | 4.42 | 47.15 |

MS, m/z 175(M+H)$^+$

| UV | neutral | anion |
|---|---|---|
| $\lambda_{max}$(nm) | 258 | 270 |
| $\lambda_{min}$(nm) | 230 | 242 |
| $\epsilon_{max}$ | 12,400 | 12,500 |
| $\epsilon_{260}$ | 12,400 | 9600 |

$pK_a=7.9$ (determined spectrophotometrically).

$^1H$-NMR (DMSO-$d_6$, 300 MHz). δ(ppm): 13.617 (broad s, 1H, N-$\underline{H}$), 9.120 (broad s, 1H, N$\underline{H}_2$), 8.402 and 8.358 (two s, 2H, C(2)-$\underline{H}$ and C(8)-$\underline{H}$), 7.750 (broad s, 1H, N$\underline{H}_2$) and 2.447 (broad s, 2H, B$\underline{H}_2$). $N^7$-cyanoborano-adenine elemental analysis (calculated for $C_6H_7BN_6 \cdot 0.25H_2O$):

|  | % Carbon | % Hydrogen | % Nitrogen |
|---|---|---|---|
| calculated | 40.37 | 4.24 | 47.09 |
| found | 40.59 | 4.43 | 47.16 |

MS, m/z 175(M + H)$^+$

| UV | cation | neutral | anion |
|---|---|---|---|
| $\lambda_{max}$(nm) | 262 | 262 | 272 |
| $\lambda_{min}$(nm) | 230 | 238 | 236 |
| $\epsilon_{max}$ | 12,300 | 12,800 | 11,900 |
| $\epsilon_{260}$ | 12,300 | 11,400 | 9,700 |

$pKa_1=1.9$. $PKa_2=5.4$ (determined spectrophotometrically).

$^1H$-NMR(DMSO-$d_6$, 300 MHz). δ(ppm): ~14.500 (broad s, 1H, N-$\underline{H}$), 8.479 and 8.440 (two sharp s and a broad flat one around the above two, 3H, C(2)-$\underline{H}$, C(8)-$\underline{H}$ and N$\underline{H}_2$), ~6.900 (broad s, 1H, N$\underline{H}_2$) and ~2.600 (broad s, 2H, B$\underline{H}$2).

$N^7$-cyanoborano-guanine $N^7$-cyanoborano-2'-deoxyguanosine (200 mg) was dissolved in $10^{-1}N$ aqueous hydrochloric acid (50 ml). The homogeneous solution was kept at room temperature for 12 days. The deposited crystals were filtered by suction, washed with ice-cold water (2×5 ml) and dried at room temperature and 1 Hgmm over $P_2O_5$ overnight. The yield was 117 mg (94.7%). $^1H$-NMR results are set forth below:

$^1$H-NMR(DMSO-d$_6$, 300 MHz). δ(ppm): 13.896 (broad s, 1H, N(9)-H̲), 11.068 (s, 1H, N(1)-H̲), 8,493 (s, 1H, C(8)-H̲), 6.716 (s, 2H, NH̲$_2$) and 2.401–2.586 (broad s, 2H, BH̲$_2$).

EXAMPLE 9

Preparation of N$^7$-cyanoborano-guanine and -adenine by Enzymatic Phosphorolysis of the Respective Nucleoside Derivatives N$^1$-cyanoborano-2'-deoxyadenosine, N$^7$-cyanoborano-2'-deoxyguanosine or N$^7$-cyanoborano-guanosine was incubated with purine nucleoside phosphorylase from calf spleen at 37° C. for 1 hour. The incubation mixture comprised 3 mM substrate in 50 mM potassium phosphate, pH 7.0, buffer (500 µL) and contained 1.1 units of the enzyme. TLC analysis (on silica gel in dichloromethane:methanol (85:15 v/v) of the incubation mixtures showed about 80–90% conversion of N$^7$-cyanoborano-2'deoxyadenosine to N$^7$-cyanoborano-adenine and approximately 10–20% conversion of the other two compounds to N$^7$-cyanoborano-guanine.

EXAMPLE 10

Synthesis of N$^3$-cyanoborano-2'-deoxyuridine by Chemical Deamination of N$^3$-cyanoborano-2'-deoxycytidine N$^3$-cyanoborano-2'-deoxycytidine (47 mg, 0.18 mmol) was dissolved in 1.0 m aqueous tripotassium phosphate solution (10 ml) at 37° C. The solution was kept at this temperature for 44 hours.

After cooling to room temperature, the solution was percolated through a DEAE-cellulose (dimethylaminoethyl cellulose) [HCO3$^-$] column (1.9×28.0 cm). The column was washed with water (850–900 ml), then with 10$^{-2}$M aqueous triethylammonium bicarbonate (pH 7.5) solution. The speed of elution was 18.4 mL/20 minutes.

The UV absorbing peak eluted by 10$^{-2}$M aqueous triethylammonium bicarbonate was pooled and evaporated to dryness. Excess triethylammonium bicarbonate was removed by repeated coevaporation with methanol. The yield was 21.0 mg of an oil, the triethylamine salt of the product.

| UV | pH 2.0 | pH 7.0 | pH 11.0 |
|---|---|---|---|
| λ$_{max}$(nm) | 264 | 264 | 264 |
| λ$_{min}$(nm) | 236 | 236 | 238 |

$^1$H-NMR(DMSO-d$_6$, 300 MHz). δ(ppm): ~8.800 (broad flat s, 1H, Et$_3$NH̲), 7.598 (d, $^3J_{HH}$=7.9 Hz, 1H, C(6)-H̲, 6.191 (t, $^3J_{HH}$=6.8 Hz, 1H, C(1')-H̲, 5.434 (d, $^3J_{HH}$=7.9 Hz, 1H, C(5)-H̲), 5.187 (d, $^3J_{HH}$=4.1 Hz, 1H, C(3') OH̲), 4.944 (t, $^3J_{HH}$=5.2 Hz, 1H, C(5') -OH̲), 4.173–4.192 (m, 1H, C(3')-H̲), 3.708–3.742 (m, 1H, C(4')-H̲), 3.498–3.538 (m, 2H, C̲(5')-H̲$_2$), 3.088 (g, $^3J_{HH}$=7.2 and 14.5 Hz, 6H, NH(CH$_2$CH$_3$)$_3$), 1.929–2.066 (m, 4H, C(2')-H$_2$+BH̲$_2$) and 1.161 (t, $^3J_{HH}$=7.2 Hz, 9H, NH (CH$_2$CH̲$_3$)$_3$.

EXAMPLE 11

Synthesis of Oligonucleotides

Oligonucleotides, Linker-5'-GCGGTGACCCG-GGAGATCTGAATTC-3', LC17-5'-GGCCCTCTAGACTTAAG-3', and SS20 were synthesized on an ABI 380B automatic DNA synthesizer, purified on 20% polyacrylamide gels, and visualized by UV shadowing. Bands were cut from the gels and the DNA was electrocuted, ethanol precipitated, and resuspended in TE (10 mM Tris, pH 7.7, 0.1 mM EDTA). Primers were end labeled with $^{35}$S by T4 polynucleotide kinase (New England Biolabs). Linker/LC17 complexes (T$_m$=62° C. in NT buffer: 50 mM Tris, pH 7.5, 10 mM MgSO$_4$, 0.1 mM DTT, 50 µg/mL BSA, Maniatis, et al.) were annealed in NT buffer by heating to 95° C. then cooling to room temperature.

Denaturing PAGE: Extended primer/template complexes were denatured at 95° C. for one minute, cooled immediately on ice, and loaded onto a 10% polyacrylamide, 7M urea gel (20 cm×40 cm×0.4 mm). Electrophoresis was performed at 75 Watts for 2 hours in TBE buffer. Following electrophoresis, the gel was soaked in 10% methanol, 10% acetic acid for 10 minutes and transferred to Whatman 3MM chromatography paper, and dried under vacuum for 1 hour, 30 minutes. The dried gel was exposed to Kodak XAR-2 X-ray film for from 1 to 5 days. Bands whose intensities lay in the linear response range of the film were integrated by scanning densitometry on an LKB 2222 laser densitometer.

Rates of incorporation were determined by dividing the amount of incorporated nucleotide (I$_1$) by the average amount of substrate present (I$_0$+0.5$_{(1)}$)) during the interval t. Rates were expressed as % incorporation per time interval=100(I$_1$)/[I$_0$+0.5(I$_1$)]t. Time course experiments demonstrated steady state conditions for the utilized primer/template to enzyme ratio (approximately 3000:1) and care was taken to reject any I$_1$>0.2-0(I$_0$) so as to assure steady state conditions (Petruska et al., *Proc. Nat'l. Acad. Sci. USA* 85, 6252–6256 (1988)).

Incorporation into M13: Primer SS20 was 5' labeled with $^{35}$S and annealed to a single stranded (−)M13 DNA template in NT by heating to 95° C., incubating at 60° C. for 10 minutes, then cooling on ice. Primer/template complexes (8 pmol), dNTPs (83 mM), dGTP or boronated 2'-deoxyguanosine-triphosphate ("dG$^B$TP") (83 mM), and Sequenase (6.5 units) were mixed and allowed to react for 15 minutes at room temperature and stopped by heating at 70° C. for ten minutes.

DMS (dimethyl sulfide) Cleavage: Extended M13 primer/template complexes (1 pmol) were exposed to 20 mM DMS for 10 minutes on ice. Reactions were stopped with 100 mM DTT.

Electrophoresis: Samples, unless otherwise noted, were mixed with an equal volume of stop solution and loaded onto 8% polyacrylamide, 7M urea gels, using TBE buffer, and run for 2 hours at 75 Watts.

Incorporation directed by M13 template: We compared the incorporation of dG$^B$TP and dGTP into a duplex by Sequenase (modified T7 DNA polymerase which has no 3'-0.5' proofreading exonuclease activity). Extension was of a synthetic primer, ss20, annealed to the (−) strand of M13. The dG$^B$TP was clearly incorporated into the extending primer as directed by the M13 template, but not as efficiently as dGTP. dGTP products extended well into the upper ranges of the gel (500 to several thousand base pairs) (data not shown). dG$^B$TP was incorporated into duplexes extending to hundreds of base pairs; however, there were numerous stalls of polymerization along the way. Clearly single dG$^B$TP incorporations did not slow the growing strand significantly under these conditions as evidenced by the lack of extension products terminating at positions occupied by single boronated guanosines; however, there were pronounced stalls at positions which required incorporation of three or more consecutive dG$^B$TP incorporations. For example, there are intense bands at position 65 whose sequence ends with GpGpGp.

Using Klenow fragment as polymerase at 37° C., no stalls were observed after three G's in a row. Taq polymerase could also be used for the incorporation of boronated dG$^B$TP into oligonucleotides at 72° C.

DMS protection: DMS methylates preferentially the N7 position of deoxyguanosine. Treatment by DMS of the duplex M13 extension products which contain either guanosine or boronated guanosine, followed by heating, results in cleavage of duplexes containing dG but no cleavage of duplexes containing dG$^B$ (data not shown). Since dG$^B$TP, which is substituted at N7, is clearly inhibiting methylation at N7, we conclude that the duplexes retain the cyanoborane at N7 during incorporation and primer extension.

EXAMPLE 12

Restriction Digestion

We used the extension product duplexes from the M13-directed synthesis to examine the ability of dG$^B$TP to act as a substrate for endonucleases. Extended M13 primer/template complexes (1 pmol) were digested by EcoRI, HaeIII, PvuI, PvuII, and Sau3AI in the manufacturer supplied buffer at 37° C. for 20 minutes.

EcoRI cuts cites occupied by dG$^B$ nearly as well as those containing dG. HaeIII, PvuI, and PvuII are clearly inhibited by dG$^B$, but the extent of inhibition cannot be precisely defined because the stall cites in the extension products coincide with the endonuclease recognition sites. Sau3AI is completely inhibited by the presence of dG$^B$. The primer, ss20, contains a SauAI recognition which would, of course, contain unmodified dG. The unmodified site serves an internal control and since the unmodified site is cleaved while site containing dG$^B$ is not cleaved, we can safely conclude that the cyanoborane at N7 is responsible for the inhibition of Sau3AI.

EXAMPLE 13

Cytotoxic Activity

The compounds prepared in accordance with the preceding examples were tested for cytotoxic activity by preparing a 1 mM solution of an adduct in 0.5% TWEEN ® 80/H$_2$O solution by homogenization. The resulting drug solutions were sterilized by passage through an Acrodisc 45 μM sterilizer.

The following cell lines were maintained in accordance with literature techniques (literature sources indicated parenthetically after identification of the cell line): murine L$_{1210}$ lymphoid leukemia (Geran et al., Cancer Chemotherapy Reports 3, 7-9 (1972)); human Tmolt$_3$ acute lymphoblastic T cell leukemia (Minowada et al., J. Nat. Cancer. Int. 49, 891-895 (1972)); colorectal adenocarcinoma SW480 (Liebovitz et al., Cancer Res. 36, 4562-4569 (1976)); lung bronchogenic MB-9812 (Aaronson et al., Expt. Cell Res. 61, 1-5 (1970)); osteosarcoma TE418 (Smith et al., Int. J. Cancer 17, 219-234 (1976)); KB epidermoid nasal pharynx (Geran et al., Ibid; Eagle, H., Proc. Soc. Expt. Biol. 89, 362-364 (1955)); HeLa-S$^5$ suspended cervical carcinoma (Puck et al., J. Exp. Med. 103, 273-283 (1956)); human lung A549 maintained in DMEM+10% fetal calf serum+G-K; HELA solid tumor maintained in EMEM+10% fetal calf serum+G-K; epiderm A431; UMR 106 in DMEM+10% fetal calf serum+antibiotics; and ileum HCT in RPMI+10% horse serum+sodium pyruvate-+antibiotics.

The protocol used to assess cytotoxicity was that of Geran, et al., Cancer Chemotherapy Reports 3, 7-9 (1972). Standards were determined in each cell line. Values are expresses for the cytotoxicity of the drug as ED$_{50}$ in μg/ml, i.e., the concentration which inhibits 50% of the cell growth determined by the trypan blue exclusion technique. Solid tumor cytotoxicity was determined by the method of Huang, et al., J. Pharm. Sci. 61, 108-110 (1972). Erlich ascites carcinoma in vivo tumor screens were conducted in CF$_1$ male mice ~28 grams) with test drugs at 8 mg/kg/day I.P. by the method of Geran et al., supra. 6-mercaptopurine was used as an internal standard.

The results of the cytotoxicity tests are set out in Table 2 below for the compounds adenine-N$^1$-cyanoborane (1), adenine-N$^7$-cyanoborane (3), guanine-N$^7$-cyanoborane (4), 9-β-D-arabinofuranosyladenine-N$^7$-cyanoborane (12), 9-β-D-arabinofuranosyladenine-N$^1$-cyanoborane (13), as well as 5FU, araC, hydroxyurea, cycloleucine, and 6MP.

In murine L-1210, most compounds showed activity.

In the human tissue culture lines, most of the compounds demonstrated good activity against Tmolt$_3$ leukemia, HELA solid tumor and colon SW480. Compounds 1 and 3 were also active against the growth of Epiderm A431 and KB nasopharynx. None of the compounds were active against UMR 106. In HeLa-S$^3$, compound 1 showed good activity. Compound 12 was active against the growth of osteosarcoma.

TABLE 2

Cytotoxic and Antitumor Activity

| Compound | In Vivo % Inhibition Ehrlick Ascites Carcinoma | Murine L$_{1210}$ | HUMAN Tmolt$_3$ | Epiderm A431 | KB | HeLa-S$^3$ | HELA | Colon SW480 | Ileum HCT | Lung MB-9812 | Lung A549 | UMR 106 | Osteosarcoma |
|---|---|---|---|---|---|---|---|---|---|---|---|---|---|
| 1 | 40.4 | 1.29 | 1.98 | 3.18 | 2.86 | 2.77 | 0.98 | 1.61 | 7.98 | 6.02 | 4.09 | 7.72 | — |
| 3 | 50.3 | 1.89 | 2.46 | 3.70 | 3.65 | 5.07 | 2.86 | 3.17 | 7.88 | 6.74 | 5.15 | 7.88 | — |
| 4 | 40.3 | 1.59 | 1.51 | 6.19 | 3.82 | 5.33 | 1.38 | 1.08 | 7.84 | 6.69 | 5.07 | 7.88 | — |
| 12 | — | — | — | — | — | — | — | — | 2.51 | — | — | — | 0.92 |
| 13 | — | — | — | — | — | — | — | — | 7.64 | — | — | — | 5.18 |
| 6MP | 99 | | | | | | | | | | | | |

| Compound | E.A. | Murine L$_{1210}$ | Tmolt$_3$ | Human Epiderm A431 | KB | HeLa-S$^3$ | HELA | Colon SW480 | Compound | Ileum HCT | Lung MB-9812 | Lung A549 | UMR 106 | Osteosarcoma |
|---|---|---|---|---|---|---|---|---|---|---|---|---|---|---|
| 5FU | | 1.41 | 2.14 | | 1.25 | 2.47 | | 3.09 | 5FU | 5.64 | | | | |
| AVAC | | 2.76 | 2.67 | | 2.54 | 2.13 | | 3.42 | ARAC | 7.24 | | | | |

TABLE 2-continued

| | | Cytotoxic and Antitumor Activity | | | | | |
|---|---|---|---|---|---|---|---|
| Hydroxy-urea | 2.67 | 3.18 | 5.29 | 1.96 | 4.74 | Hydroxy-urea | 7.33 | 7.57 |
| Cyclo-leucine | 3.08 | 2.38 | 5.74 | 2.38 | 3.81 | Cyclo-leucine | 4.36 | 6.18 |

EXAMPLE 14

Anti-inflammatory Activity $CF_1$ male mice (~25 grams) were administered test drugs at 8 mg/kg in 0.0% TWEEN ® 80-$H_2O$ intraperitoneally 3 hours and again 30 minutes prior to the injection of 0.2 ml of 1% carrageenan in 0.9% saline into the plantar surface of the right hind foot. Saline was injected into the left hind foot which serves as a base line. After 3 hours, both feet were excised at the tibiotarsal (ankle) joint according to the modified method of Winter (Winter et al., Proc. Soc. Biol. Med. 175, 435–442 (1970). The control mice afforded a 78±3 mg increase in paw weight. Data are present below in Table 3:

TABLE 3

| The Anti-Inflammatory Activity of Boron Compounds in Mice ($CF_1$) at 8 mg/kg | |
|---|---|
| Compound | % of Control |
| 1 | 56.3 |
| 3 | 49.1 |
| 4 | 50.9 |
| Standard Indomethacin (10 mg/kg) | 74 |

EXAMPLE 15

Hypolipidemic Activity

Test compounds were suspended in an aqueous 1% carboxymethylcellulose solution, homogenized, and administered to $CF_1$ male mice (~25 grams) intraperitoneally for 16 days. On days 9 and 16, blood was obtained by tail vein bleeding, and the serum was separated by centrifugation for 3 minutes. The serum cholesterol levels were determined by a modification of the Liebermann-Burchard reaction (Ness et al., Clin. Chim. Acta. 10, 229–237 (1964)). Serum was also analyzed for triglyceride content by a commercial kit (BioDynamics/bmc) using a BMC single vial triglycerides colorimetric method 348201. Food and water were available ad libitum for animals in the experiments. Test results are set forth in

TABLE 4

| | Hypolipidemic Activity in $CF_1$ Mice at 8 mg/kg/day I.P. | | |
|---|---|---|---|
| | Percent of Control | | |
| | Serum Cholesterol | | Serum Triglycerides |
| (N = 6) Control | Day 9<br>100 ± 6 | Day 16<br>100 ± 5 | Day 16<br>100 ± 7 |
| Compound | | | |
| 1 | 90 | 73 | 107 |
| 3 | 106 | 74 | 86 |
| 4 | 89 | 73 | 65 |
| 12 | 48 | 49 | 64 |
| 13 | 46 | 55 | 66 |
| Standard Clofibrate (150 mg/kg/day) | 88 | 86 | 75 |

EXAMPLE 16

Analgesic Activity

Compounds were tested for analgesic activity by the tail flick test (Hall et al., J. Pharm. Sci. 69, 1451–1452 (1980) and Dewey et al., J. Pharmacol. Exp. Ther. 175, 435 (1970)) and writhing reflex (Hall et al., J. Pharm. Sci. 69, 1451–1452 (1980) and Hendershot et al., J. Pharmacol. Exp. Ther. 125, 237 (1959)).

In the tail flick test, male $CF_1$ mice were administered test drugs at 8 mg/kg i.p. 5 minutes prior to the analgesic test, and the tail flick response time was measured. In the writhing test, male mice were administered the test drugs at 8 mg/kg i.p. 20 minutes prior to the administration of 0.5 ml of 0.6% acetic acid. After 5 minutes, the number of stretches, characterized by repeated contractures, was counted for ten minutes. The results of the test are set forth below in Table 5.

TABLE 5

| Analgesic Activity of Boron Compounds in Mice at 8 mg/kg | | |
|---|---|---|
| Compound | Writhing<br>% Control | Tail Flick<br>Response Time<br>% Increase |
| 1 | 13 | 147 |
| 3 | 18 | 151 |
| 4 | 59 | 142 |
| Standards:<br>Indomethacin<br>(10 mg/kg) | 43 | — |
| Morphine (1 mg/kg) | — | 210 |

EXAMPLE 17

Use of 2'-deoxyguanosine-$N^7$-cyanoborane-5'-triphosphate in Polymerase Chain Reaction (PCR)

Boronated Triphosphate (dG$^B$TP) along with dATP, dCTP, and dTTP were used to PCR amplify a 265 base pair fragment of M13 DNA between 2 oligonucleotide primers (primer 1 equivalent to positions 6200–6221, and primer 2 complementary to positions 6466–6477). Reaction conditions were: 50 mM KCl, 10 mM Tris pH 8.3, 1.5 mM $MgCl_2$, 0.2 pM primers 1 and 2, 5 mM double stranded M-13 template, 5 units Taq DNA polymerase and either 50 μM dNTP or 100 μM dATP, dCTP, dTTP, dG$^B$TP in a 100 μl reaction volume. PCR was carried out by 25 cycles of: 94° C. (10 seconds)→56° C. (10 μs)→72° C. (2 minutes).

Following amplification, 10 μl of the reaction mixture was analyzed on a 4% agarose gel. Results indicate that a predominant 265 base pair band was produced using either dGTP or dG$^B$TP as a substrate.

Stable incorporation of dG$^B$TP was configured by PvuII restriction analysis of the PCR product. The product produced from dGTP as a substrate was completely cleared by PvuII whereas the product from dG$^B$TP was 90% resistant to PvuII cleavage, confirming the presence of boronated nucleoside in the PCR generated oligomer.

That which is claimed is:

1. A boronated base selected from the group consisting of purines and pyrimidines, which base is N-boronated with a boron-containing substituent selected from the group consisting of —$BH_2CN$, —$BH_3$, —$BF_3$, —$BH_2COOR$ and —$BH_2C(O)NHR$, wherein R is hydrogen or $C_1$ to $C_{18}$ alkyl.

2. A boronated base according to claim 1 wherein said base is selected from the group consisting of adenine, cytosine, guanine, and inosine.

3. A boronated base according to claim 1 wherein said boron-containing substituent is —$BH_2CN$.

4. A boronated base according to claim 1 wherein said boronated base is adenine-$N^1$-cyanoborane; adenine-$N^3$-cyanoborane; adenine-$N^7$-cyanoborane; guanine-$N^7$-cyanoborane; cytosine-$N^3$-cyanoborane; hypoxanthine-$N^7$-cyanoborane; 5-methylcytosine-$N^3$-cyanoborane; 9-benzyladenine-$N^1$-cyanoborane; 9-ethyladenine-$N^1$-cyanoborane; 9-[(2-hydroxyethoxy)methyl]guanine-$N^7$-cyanoborane; or 9-hydroxyethylguanine-$N^7$-cyanoborane.

5. A boronated base according to claim 1, wherein said boronated base is adenine-$N^1$-cyanoborane.

6. A boronated base according to claim 1, wherein said boronated base is adenine-$N^3$-cyanoborane.

7. A boronated base according to claim 1, wherein said boronated base is adenine-$N^7$-cyanoborane.

8. A boronated base according to claim 1, wherein said boronated base is guanine-$N^7$-cyanoborane.

9. A boronated base according to claim 1, wherein said boronated base is cytosine-$N^3$-cyanoborane.

10. A boronated base according to claim 1, wherein said boronated base is hypoxanthine-$N^7$-cyanoborane.

11. A boronated base according to claim 1, wherein said boronated base is 5-methylcytosine-$N^3$-cyanoborane.

12. A boronated base according to claim 1, wherein said boronated base is 9-benzyladenine-$N^1$-cyanoborane.

13. A boronated base according to claim 1, wherein said boronated base is 9-ethyladenine-$N^1$-cyanoborane.

14. A boronated base according to claim 1, wherein said boronated base is 9-[(2-hydroxyethoxy)methyl]guanine-$N^7$-cyanoborane.

15. A boronated base according to claim 1, wherein said boronated base is 9-hydroxyethylguanine-$N^7$-cyanoborane.

16. A pharmaceutical formulation comprising an effective antihyperlipidemic, antiinflammatory or analgesic amount of a boronated compound in a pharmaceutically acceptable carrier, said boronated compound comprising a boronated purine or pyrimidine base which is N-boronated with a boron-containing substituent selected from the group consisting of —$BH_2CN$, —$BH_3$, —$BF_3$, —$BH_2COOR$ and —$BH_2C(O)NHR$, wherein R is hydrogen or $C_1$ to $C_{18}$ alkyl.

17. A pharmaceutical formulation according to claim 16, wherein said base is selected from the group consisting of adenine, cytosine, guanine, and inosine.

18. A pharmaceutical formulation according to claim 16, wherein said boron-containing substituent is —$BH_2CN$.

19. A pharmaceutical formulation according to claim 16, wherein said boronated base is adenine-$N^1$-cyanoborane; adenine-$N^3$-cyanoborane; adenine-$N^7$-cyanoborane; guanine-$N^7$-cyanoborane; cytosine-$N^3$-cyanoborane; hypoxanthine-$N^7$-cyanoborane; 5-methylcytosine-$N^3$-cyanoborane; 9-benzyladenine-$N^1$-cyanoborane; 9-ethyladenine-$N^1$-cyanoborane; 9-[(2-hydroxyethoxy)methyl]guanine-$N^7$-cyanoborane; or 9-hydroxyethylguanine-$N^7$-cyanoborane.

20. A pharmaceutical formulation according to claim 16, wherein said boronated base is adenine-$N^1$-cyanoborane.

21. A pharmaceutical formulation according to claim 16, wherein said boronated base is adenine-$N^3$-cyanoborane.

22. A pharmaceutical formulation according to claim 16, wherein said boronated base is adenine-$N^7$-cyanoborane.

23. A pharmaceutical formulation according to claim 16, wherein said boronated base is guanine-$N^7$-cyanoborane.

24. A pharmaceutical formulation according to claim 16, wherein said boronated base is cytosine-$N^3$-cyanoborane.

25. A pharmaceutical formulation according to claim 16, wherein said boronated base is hypoxanthine-$N^7$-cyanoborane.

26. A pharmaceutical formulation according to claim 16, wherein said boronated base is 5-methylcytosine-$N^3$-cyanoborane.

27. A pharmaceutical formulation according to claim 16, wherein said boronated base is 9-benzyladenine-$N^1$-cyanoborane.

28. A pharmaceutical formulation according to claim 16, wherein said boronated base is 9-ethyladenine-$N^1$-cyanoborane.

29. A pharmaceutical formulation according to claim 16, wherein said boronated base is 9-[(2-hydroxyethoxy)methyl]guanine-$N^7$-cyanoborane.

30. A pharmaceutical formulation according to claim 16, wherein said boronated base is 9-hydroxyethylguanine-$N^7$-cyanoborane.

* * * * *